United States Patent [19]

Reinehr

[11] 4,213,901
[45] Jul. 22, 1980

[54] 1-AZA-1,5,9-CYCLODODECATRIENES

[75] Inventor: Dieter Reinehr, Kandern, Fed. Rep. of Germany

[73] Assignee: Ciba-Geigy Corporation, Ardsley, N.Y.

[21] Appl. No.: 923,437

[22] Filed: Jul. 10, 1978

[30] Foreign Application Priority Data

Jul. 19, 1977 [CH] Switzerland ............ 8913/77

[51] Int. Cl.² .......................... C07D 225/02
[52] U.S. Cl. ................ 260/239 BE; 71/121;
260/563 R; 260/566 R; 260/584 R; 260/584 A;
424/325; 585/22; 585/23; 585/369
[58] Field of Search ................. 260/239 BE

[56] References Cited

U.S. PATENT DOCUMENTS 3,939,147 2/1976 Hugelin et al. .............. 260/239 BC

Primary Examiner—Alton D. Rollins
Attorney, Agent, or Firm—Michael W. Glynn

[57] ABSTRACT

Compounds of the formula

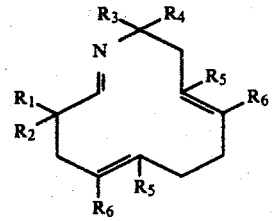

and a process for their preparation by reacting azabutadienes with dienes, especially 1,3-butadiene, in the presence of catalysts are described. In the formula I, $R_1$ and $R_3$ independently of one another are hydrogen or alkyl having 1–8 C atoms and $R_2$ and $R_4$ independently of one another are alkyl having 1–8 C atoms, or $R_1$ and $R_2$ and/or $R_3$ and $R_4$ together with the bonding C atom form a cycloaliphatic ring having 4–8 C atoms, and $R_5$ and $R_6$ independently of one another are hydrogen or alkyl having 1–4 C atoms. The compounds of the formula I are valuable intermediates for the preparation of active compounds for combating plant pests.

10 Claims, No Drawings

1-AZA-1,5,9-CYCLODODECATRIENES

The present invention relates to novel 1-aza-1,5,9-cyclododecatrienes and a process for their preparation.

It is known from German Offenlegungsschrift No. 2,330,087 that 1,2-diaza-1,5,9-cyclododecatrienes can be prepared by reacting 1,3-diolefins with azines in the presence of a catalyst which is obtained by reducing a carbonyl-free nickel compound in the presence of a chelating olefin and in the presence of an electron donor.

It has now been found that novel unsaturated heterocyclic compounds, i.e. 1-aza-1,5,9-cyclododecatrienes of the formula I

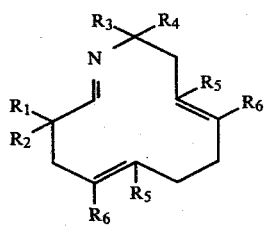

(I)

in which $R_1$ and $R_3$ independently of one another are hydrogen or alkyl having 1–8 C atoms and $R_2$ and $R_4$ independently of one another are alkyl having 1–8 C atoms, or $R_1$ and $R_2$ and/or $R_3$ and $R_4$ together with the bonding C atom form a cycloaliphatic ring having 4–8 C atoms, and $R_5$ and $R_6$ independently of one another are hydrogen or alkyl having 1–4 carbon atoms, can be prepared by reacting an aza-butadiene of the formula II

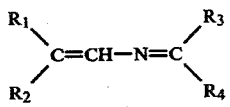

(II)

in which $R_1$ to $R_4$ are as defined under formula I, in the presence of a catalyst which is obtained by reducing a carbonyl-free nickel compound in the presence of a chelating olefin and if appropriate in the presence of an electron donor, at a temperature between about $-40°$ C. and $+150°$ C. with a compound of the formula III

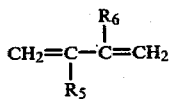

(III)

in which $R_5$ and $R_6$ are as defined under formula I.

Alkyl groups $R_1$ to $R_4$ can be straight-chain or branched. Alkyl groups $R_5$ and $R_6$ are preferably straight-chain and have 1 or 2 C atoms. Alkyl groups $R_1$ to $R_3$ preferably have 1–5 C atoms and alkyl groups $R_4$ preferably have 1–7 C atoms. Examples of alkyl groups $R_1$ to $R_6$ are: the methyl, ethyl, n-propyl, isopropyl, n-, sec.- and tert.-butyl, n-pentyl, 2- or 3-pentyl, n-hexyl, 3-heptyl and n-octyl groups.

If $R_1$ and $R_2$ and/or $R_3$ and $R_4$ together with the bonding C atom form a cycloaliphatic ring, this is in particular an unsubstituted cycloalkyl ring having 5–8 C atoms. Preferably, the said substituents, together with the bonding C atom, form a cyclopentyl or cyclohexyl group.

Preferred compounds of the formula I are those in which $R_5$ and $R_6$ are each hydrogen, $R_1$ and $R_3$ independently of one another are hydrogen or alkyl having 1–5 C atoms, $R_2$ is alkyl having 1–5 C atoms and $R_4$ is alkyl having 1–7 C atoms, or in which $R_3$, $R_5$ and $R_6$ are each hydrogen, $R_1$ and $R_2$ together with the bonding C atom are cyclopentyl or cyclohexyl and $R_4$ is alkyl having 1–7 C atoms.

Particularly preferred compounds are those of the formula I in which $R_3$, $R_5$ and $R_6$ are each hydrogen, $R_1$ and $R_2$ independently of one another are alkyl having 1–4 C atoms, especially methyl, ethyl, n-propyl or n-butyl, or together with the bonding C atom are cyclohexyl, and $R_4$ is alkyl having 1–7 C atoms, especially ethyl, iso-propyl, tert.-butyl, 2- or 3-pentyl or 3-heptyl.

The aza-butadienes of the formula II are known in some cases and can be prepared, for example, as follows:

By reacting ketones of the formula

with allylamine to give aza-butadienes of the formula II, in which $R_1$ is hydrogen and $R_2$ is methyl and $R_3$ and $R_4$ are as defined. With this process, in the main compounds of the formula IV

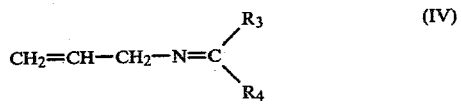

(IV)

are formed initially and these can be isomerised in the presence of suitable catalysts, such as $K_2O/Al_2O_3$ catalysts, at elevated temperatures, to give aza-butadienes of the formula II in which $R_1$ to $R_4$ are as defined above.

By reacting aldehydes of the formula

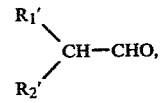

in which $R_1'$ and $R_2'$ are alkyl groups having 1–8 C atoms or together with the bonding C atom are a cycloaliphatic ring having 4–8 C atoms, with ammonia to give compounds of the formula V

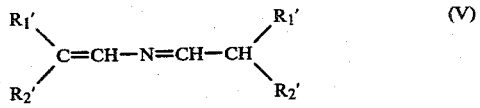

(V)

and, if desired, further reacting the compounds of formula V with suitable aldehydes or ketones.

By isomerising compounds of the formula VIa or VIb

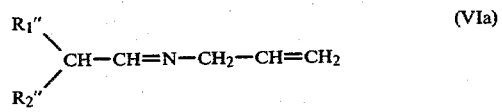

(VIa)

or

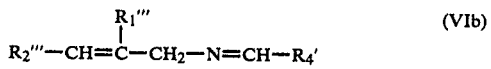 (VIb)

in which $R_1''$ and $R_2''$ independently of one another are alkyl having 1–8 C atoms or together with the bonding C atom are a cycloaliphatic ring having 4–8 C atoms, $R_1'''$ is hydrogen or alkyl having 1–8 C atoms, $R_2'''$ is hydrogen or alkyl having 1–7 C atoms and $R_4'$ is tertiary alkyl having 4–8 C atoms, at temperatures between about 0° and 80° C. and preferably about 10°–50° C., in the presence of an inert organic solvent, for example anhydrous benzene or toluene, and in the presence of an alkali metal alcoholate or alkaline earth metal alcoholate, such as sodium tert.-butylate or potassium tert.-butylate.

When compounds of the formula VIa are used, aza-butadienes of the formula II are formed in which $R_1$ and $R_2$ independently of one another are alkyl having 1–8 C atoms or together with the bonding C atom are a cycloaliphatic ring having 4–8 C atoms, $R_3$ is hydrogen and $R_4$ is ethyl. When compounds of the formula VIb are used, on the other hand, aza-butadienes of the formula II are obtained in which $R_1$ is hydrogen or alkyl having 1–8 C atoms, $R_2$ is alkyl having 1–8 C atoms, $R_3$ is hydrogen and $R_4$ is tertiary alkyl having 4–8 C atoms.

The compounds of the formula VIa or VIb can, in turn, be prepared in a manner known per se by reacting aldehydes

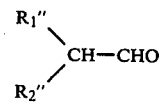

with allylamine or by reacting an amine of the formula

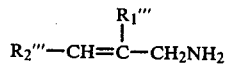

with an aldehyde of the formula $R_4'$—CHO.

The starting compounds of the formula III are known or can be prepared in a manner known per se. Compounds preferably used are 2,3-dimethyl-1,3-butadiene and isoprene, but especially 1,3-butadiene.

The catalysts which can be used in the process according to the invention are known per se. Examples of suitable carbonyl-free nickel compounds are chelates or salts of inorganic and organic acids, such as nickel halides, for example nickel chloride, nickel iodide and nickel boride, nickel cyanide, nickel acetylacetonate, nickel benzoylacetonate, nickel carbonate, nickel formate, nickel acetate, nickel stearate, nickel oxalate, nickel benzoate, nickel sulphate and nickel dimethylglyoxime. The nature of the anion in the carbonyl-free nickel compounds is not important. For reasons of accessibility and because of the good solubility in aprotic solvents, however, nickel stearate and nickel acetylacetonate are preferred.

Chelating olefins for the preparation of the catalysts which can be used according to the invention are, for example, ethylene and cyclic olefins with isolated double bonds, such as c,c-1,5-cyclooctadiene and t,t,c- or t,t,t-1,5,9-cyclododecatriene, but in particular conjugated dienes and tetraenes, such as the starting compounds of the formula III and 2c,4t- or 2t,4t-hexadiene, 1,3-cyclooctadiene and cyclooctatetraene.

The electron donors (ligands) employed are Lewis bases, such as alkyl- or aryl-phosphines, alkyl phosphites or aryl phosphites and also the corresponding compounds of arsenic and antimony, for example triethylphosphine, tri-n-butylphosphine, triphenylphosphine, triethylarsine, triphenylarsine, triphenyl-antimony, triphenyl phosphite, tri-n-butyl phosphite, tris-o-cresyl phosphite, tris-o-methoxyphenyl phosphite, o-biphenyl-diphenyl phosphite and tris-o-biphenyl phosphite. Alkyl- or aryl-phosphines and alkyl phosphites or aryl phosphites are preferably used. Triphenylphosphine and triphenyl phosphite are particularly preferred.

The preparation of the catalyst is usually carried out in situ by reducing the carbonyl-free nickel compound, if desired in the presence of the electron donor, in an inert organic solvent which already contains the starting material of the formula III. The reduction can be carried out by adding a reducing agent, such as halogen-free metal-organic compounds, especially halogen-free metal-alkyls or metal-aryls, or by an electrolytic route. The preferred method is the reduction of the carbonyl-free nickel compound in situ with halogen-free metal-alkyls or metal-aryls in the presence of an electron donor, especially the preferred electron donors mentioned above. On the other hand, it is also possible to use a previously isolated nickel-(O) complex, such as the ethylene-bis-(triphenylphosphine)-nickel-(O) complex, the bis-cyclo-octa-1,5-diene-nickel-(O) complex of the trans-cyclodo-deca-1,5,9-triene-nickel-(O) complex, for the reaction of the aza-butadiene of the formula II with the compounds of the formula III. Nickel-(O) complex catalysts of this type can be prepared in a known manner, again by reduction of a carbonyl-free nickel compound in the presence of a suitable chelating olefin of the abovementioned type and if desired in the presence of an electron donor (ligand), for example an alkyl- or aryl-phosphine.

Halogen-free metal-alkyls or metal-aryls are, for example, phenyl or alkyl compounds of lithium, gallium, magnesium or zinc, having up to 8 C atoms in the alkyl moieties, such as phenyl-lithium, methyl-lithium, n-butyl-lithium, tri-n-butyl-gallium, dimethyl-magnesium and diethyl-zinc, but in particular trialkyl-aluminium and dialkyl-alkoxy-aluminium compounds having up to 8 C atoms in the alkyl moieties and 1 or 2 C atoms in the alkoxy moieties, for example trimethyl-aluminium, triethyl-aluminium, tri-n-butyl-aluminium, tri-n-octyl-aluminium and ethoxydiethyl-aluminium. The use of ethoxydiethyl-aluminium as the reducing agent has proved particularly advantageous.

When the preparation is carried out in situ, the nickel compound and the electron donor are advantageously used in a mutual molar ratio of 1:1 to 1:3, whilst the reducing agent is employed in an approximately 2-fold to 10-fold excess, based on the nickel compound.

The reaction according to the invention is advantageously carried out in the presence of an inert organic aprotic solvent. Such solvents are, in particular, aliphatic or aromatic hydrocarbons, which can be halogenated, or aliphatic and cyclic ethers, such as n-hexane, n-heptane, benzene, toluene, chlorobenzene, methylene chloride, diethyl ether and dioxan. Particularly, preferentially, the reaction is carried out in an anhydrous medium, in particular in anhydrous benzene or toluene.

However, it is also possible, both during the preparation of the catalyst in situ and during the subsequent reaction with the aza-butadiene of the formula II, to use an excess of the starting diolefin of the formula III as the solvent.

If the reaction is carried out in the presence of an organic solvent, it is possible to use either stoichiometric amounts of the 1,3-diolefin of the formula III and the compounds of the formula II or a slight excess of the 1,3-diolefin of the formula III, without the yield of the compound of the formula I being significantly impaired.

The reaction according to the invention can be carried out under normal pressure or under excess pressure, for example under an excess pressure of up to about 10 bars. The reaction is preferably carried out under an initial pressure of about 1 to 1.5 bars.

Although the reaction can be carried out at temperatures between −40° C. and +150° C., a temperature range of +40° C. to +110° C. is preferred.

In general, it is advisable to carry out the reaction under a blanketing gas, such as nitrogen or argon.

The compounds of the formula I obtained from the reaction can be isolated and purified in a conventional manner, for example by means of repeated distillation. The novel 1-aza-1,5,9-cyclododecatrienes of the formula I are obtained in the form of colourless to slightly yellowish liquids and can be used, for example, to prepare active compounds for combating plant pests, in particular phythopathogenic fungi.

Active compounds of this type can be prepared, for example, by converting a compound of the formula I, in an aqueous or aqueous-organic medium in the presence of an inorganic acid which is non-oxidising under the reaction conditions, to a compound of the formula VII

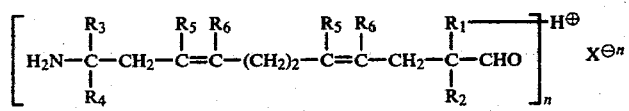

and catalytically hydrogenating the compound of the formula VII to a compound of the formula VIII

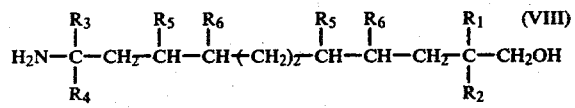

in which formulae VII and VIII $R_1$ to $R_6$ are as defined under formula I, X is the anion of an inorganic acid which is non-oxidising under the reaction conditions and n is an integer corresponding to the valency of X.

The hydrolysis to the compounds of the formula VII is advantageously carried out in an aqueous medium. Platinum-on-charcoal or palladium-on-charcoal catalysts are advantageously used for the catalytic hydrogenation to the amino-alcohols of the formula VIII.

Using the said active compounds, fungi occurring on plants or parts of plants can be controlled or destroyed. The compounds are suitable, for example, for combating phytopathogenic fungi of the categories Basidiomycetes, such as rust fungi (for example Puccinia), Fungi imperfecti (for example Cercospora) and Phycomycetes (for example Oomycetes, such as Plasmopara and Phytophthora).

Amino-alcohols of the formula VIII can also be employed as active compounds for regulating plant growth.

EXAMPLE 1

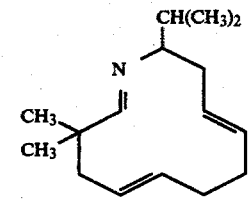

Under a blanketing gas (argon), 2.57 g (0.01 mol) of nickel actylacetonate and 1.66 g (0.01 mol) of triethyl phosphite are dissolved in 120 g of absolute toluene, after which the solution is saturated at 20°–25° C. with 1,3-butadiene. 3.9 g (0.03 mol) of ethoxydiethylaluminium are then slowly added dropwise, whilst passing in a gentle stream of 1,3-butadiene, and during the addition the original green colour changes to light red in the course of 5 minutes. The reaction mixture is heated to 60° C. and, whilst passing in a vigorous stream of 1,3-butadiene, 122.5 g (0.98 mol) of N-isobutylidene-2-methyl-propenylamine [prepared by reacting isobutyraldehyde with ammonia in accordance with J. Org. Chem. 26, 1822–25 (1961); boiling point 139°–141° C./760 mm Hg] are added dropwise in the course of 45 minutes at a rate such that the butadiene passed in is just consumed. After the dropwise addition is complete, the reaction mixture is stirred at 60° C. for a further 1 hour, whilst continuously passing in 1,3-butadiene, and then cooled to 20°–25° C. To deactivate the catalyst, 0.32 g (0.01 mol) of sulphur is added to the reaction solution and the solution is distilled. A first fraction, which in addition to 120 g of toluene also contains traces of triethyl phosphite and butadiene dimers (gas chromatogram), is obtained at a bath temperature of up to 50° C./1 mm Hg. Subsequent fine distillation yields 212.5 g (0.912 mol) of 3,3-dimethyl-12-isopropyl-1-aza-1,5,9-cyclododecatriene; yield 93% of theory, based on converted N-isobutylidene-2-methylpropenylamine (conversion 100%); boiling point 54°–55° C./0.01 mm Hg; $n_D° = 1.4832$.

Analysis for $C_{16}H_{27}N$ (molecular weight 233): calculated: C, 82.34%; H, 11.66%; N, 6.00%. found: C, 82.43%; H, 12.00%; N, 6.10%.

Mass spectrum: molecular peak 233; fragment masses 218, 190, 176, 125, 82 and 55.

$^1$H-NMR spectrum: τ(ppm): 2.94(s), 4.6–5.15(m), 7.5(m), 7.7–8.4(m), 8.85(s), 8.98(s), 9.10 and 9.16(dd) in a ratio of 1:4:1:9:3:3:6.

IR spectrum (liquid): $\nu(\text{>C=N--})$ 1,665 cm$^{-1}$

-continued

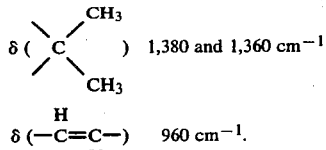  1,380 and 1,360 cm$^{-1}$ $\delta(-\underset{H}{\overset{H}{C}}=C-)$  960 cm$^{-1}$.

EXAMPLE 2

Under a blanketing gas (argon), 2.8 g (0.011 mol) of nickel acetylacetonate and 2.8 g (0.011 mol) of triphenylphosphine in 75.7 g of absolute toluene, in which 36.35 g (0.673 mol) of 1,3-butadiene have been dissolved, are reduced with 3 g (0.023 mol) of ethoxydiethyl-aluminium at 0° to 20° C. The reaction mixture is stirred for 1 hour at 20° C. and then cooled to 0° C. At this temperature, 48.1 g (0.385 mol) of N-isobutylidene-2-methyl-propenylamine [1-isopropyl-4,4-dimethyl-2-aza-1,3-butadiene] are added all at once to the above-mentioned solution. The reaction mixture is now warmed to 40° C. and kept at this temperature for 2 hours with continuous stirring. The reaction solution is then cooled to 0° C., 17.2 g (55.5 mmols) of triphenyl phosphite are added in order to deactivate the catalyst and the mixture is distilled. A first fraction, which in addition to 75.6 g of toluene also contains 5.0 g (40 mmols) of N-isobutylidene-2-methyl-propenylamine (gas chromatogram), is obtained at a bath temperature of up to 50° C./0.2 mm Hg. Subsequent fine distillation yields 4.50 g (0.193 mol) of 3,3-dimethyl-12-isopropyl-1-aza-1,5,9-cyclododecatriene; yield 55.9% of theory, based on converted 1-isopropyl-4,4-dimethyl-2-aza-1,3-butadiene (conversion 89.6%).

EXAMPLE 3

Example 1 is repeated except that the reaction temperature is raised to 90° C. and 2.8 g (0.011 mol) of triphenylphosphine are used in place of 1.66 g (0.01 mol) of triethyl phosphite. 3,3-Dimethyl-12-isopropyl-1-aza-1,5,9-cyclododecatriene is obtained, after a reaction time of 25 minutes, in a yield of 74% of theory (conversion 100%).

EXAMPLE 4

Example 2 is repeated except that 3.4 g (0.011 mol) of triphenyl phosphite are used in place of 2.8 g (0.011 mol) of triphenylphosphine. 3,3-Dimethyl-12-isopropyl-1-aza-1,5,9-cyclododecatriene is obtained in a yield of 65.2% of theory (conversion 96%).

EXAMPLE 5

Example 2 is repeated except that 1.6 g (0.01 mol) of tri-isopropylphosphine are used in place of 2.8 g (0.011 mol) of triphenylphosphine. 3,3-Dimethyl-12-isopropyl-1-aza-1,5,9-cyclododecatriene is obtained in a yield of 65.7% of theory (conversion 100%).

EXAMPLE 6

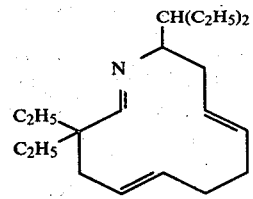

The procedure described in Example 4 is repeated except that 72.4 g (0.4 mol) of 1-(3-pentyl)-4,4-diethyl-2-aza-1,3-butadiene [prepared by reacting 2-ethylbutyraldehyde with ammonia in accordance with U.S. Pat. No. 2,319,948] and 48.4 g (0.895 mol) of 1,3-butadiene are used. After working up as described in Example 2, 56.8 g (0.197 mol) of 3,3-diethyl-12-(3-pentyl)-1-aza-1,5,9-cyclododecatriene are obtained, corresponding to a yield of 51.25 of theory, based on converted 1-(3-pentyl)-4,4-diethyl-2-aza-1,3-butadiene (conversion 96.4%); boiling point 90°-92° C./10$^{-3}$ mm Hg; n$_D^{20}$ = 1.4840.

Analysis for $C_{20}H_{35}N$ (molecular weight 289): calculated: C, 83.0%; H, 12.1%; N, 4.9%. found: C, 83.2%; H, 12.0%; N, 4.7%.

Mass spectrum: molecular peak 289; fragment masses 274, 260 and 218.

$^1$H-NMR spectrum: τ(ppm): 2.92(s), 4.6–5.2(m), 7.5–8.75(m) and 8.9–9.2(m) in a ratio of 1:4:18:12.

| IR spectrum (liquid): | $\nu(\overset{\diagdown}{\underset{\diagup}{}}C=N-)$ | 1,667 cm$^{-1}$ |
|---|---|---|
| | $\delta(-CH_3)$ | 1,375 cm$^{-1}$ |
| | $\delta(-\underset{H}{\overset{H}{C}}=C-)$ | 962 cm$^{-1}$ |

EXAMPLE 7

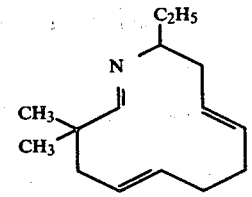

The procedure described in Example 2 is repeated except that 48.5 g (0.437 mol) of N-propylidene-(2-methylpropenylamine) [1-ethyl-4,4-dimethyl-2-aza-1,3-butadiene] and 61.0 g (1.13 mols) of 1,3-butadiene are used. Distillation yields 62.0 g (0.283 mol) of 3,3-dimethyl-12-ethyl-1-aza-1,5,9-cyclododecatriene: yield 64.9% of theory, based on converted N-propylidene-(2-methyl-propenylamine) (conversion 100%); boiling point 65°-66° C./0.005 mm Hg; n$_D^\circ$ = 1.4864.

Analysis for $C_{15}H_{25}N$ (molecular weight 219): calculated: C, 82.2%; H, 11.4%; N, 6.4%. found: C, 81.9%; H, 11.3%; N, 6.5%. Mass spectrum: molecular peak 219; fragment masses 204 and 190.

$^1$H-NMR spectrum: τ(ppm): 2.90(s), 4.5–5.2(m), 7.4(m), 7.7–8.2(m), 8.5(m), 8.88(s), 9.0(s) and 9.25(t) in a ratio of 1:4:1:8:2:3:3:3.

IR spectrum (liquid): 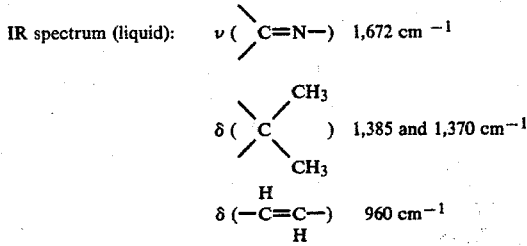

The N-propylidene-(2-methyl-propenylamine) used in the above example was prepared as follows:

25 g (0.223 mol) of potassium tert.-butylate are suspended in one litre of anhydrous diethyl ether. 921 g (8.3 mols) of isobutylidene-allylamine are then added dropwise in the course of 1 hour, with continuous stirring, at such a rate that the temperature of the reaction mixture does not rise above 20° C. After the dropwise addition is complete, the mixture is stirred for a further 5 hours at 20°–22° C. The reaction is then discontinued and the solvent is distilled over at a bath temperature of 40° C. and under a pressure of 200–50 mm Hg. The residue is distilled at a bath temperature of 70° C./0.1 mm Hg into a receiver cooled with $CO_2$/methanol. Subsequent fine distillation yields 808 g (7.93 mols) of N-propylidene-(2-methyl-propenylamine), corresponding to a yield of 87.6% of theory; boiling point 122° C.; $n_D^{20}=1.471$.

EXAMPLE 8

Example 7 is repeated except that the reaction temperature is raised to 90°–95° C. 3,3-Dimethyl-12-ethyl-1-aza-1,5,9-cyclododecatriene is obtained in a yield of 86% of theory (conversion 100%).

EXAMPLE 9

The procedure described in Example 2 is repeated except that 110 g (1.13 mols) of N-isopropylidene-propenylamine [prepared by reacting acetone with allylamine, cf. B. A. Kazanskii et al., Zhurnal Organicheskoi Khimii, Volume 6, No. 11, 2197–9 (1970)] and 108 g (2 mols) of 1,3-butadiene are used. Distillation yields 187.0 g (0.91 mol) of 3,12,12-trimethyl-1-aza-1,5,9-cyclododecatriene; yield 80.5% of theory, based on converted N-isopropylidene-propenylamine (conversion 100%); boiling point 55° C./0.03 mm Hg; $n_D^{20}=1.4895$.

Analysis for $C_{14}H_{23}N$ (molecular weight 205): calculated: C, 81.89%; H, 11.29%; N, 6.82%. found: C, 81.56%; H, 11.34%; N, 6.91%.

Mass spectrum: molecular peak 205; fragment masses 190, 97 and 82.

$^1$H-NMR spectrum: τ(ppm): 3.08(d), 4.9(m), 7.4–8.2(m), 8.72(s), 8.82(s) and 8.91(d) in a ratio of 1:4:9:3:3:3.

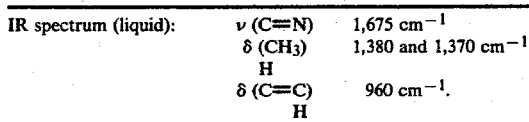

EXAMPLE 10

The procedure described in Example 2 is repeated except that 160 g (1.28 mols) of N-2,2-dimethyl-propylidene-(propenylamine) and 120 g (2.22 mols) of 1,3-butadiene are used. After a reaction time of 6 hours at 42° C., distillation yields 161 g (0.69 mol) of 3-methyl-12-tert.-butyl-1-aza-1,5,9-cyclododecatriene; yield 76.5% of theory based on converted N-2,2-dimethyl-propylidene-(propenylamine) (conversion 70.5%); boiling point 65° C./0.05 mm Hg; $n_D^{20}=1.4866$.

Analysis for $C_{16}H_{27}N$ (molecular weight 233): calculated: C, 82.34%; H, 11.66%; N, 6.00%. found: C, 82.13%; H, 11.65%; N, 6.17%.

Mass spectrum: molecular peak 233; fragment masses 218, 190, 117, 162, 125 and 82.

$^1$H-NMR spectrum τ(ppm): 3.08(d), 4.75–5.15(m), 7.4–8.2(m), 8.95(d) and 9.09(s) in a ratio of 1:4:10:3:9.

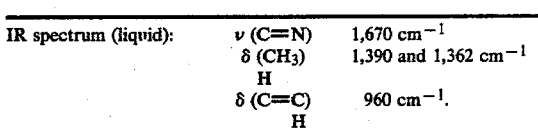

The N-2,2-dimethyl-propylidene-(propenylamine) used in the above example was prepared analogously to the N-propylidene-(2-methyl-propenylamine) according to Example 7 (cf. final paragraph of Example 7) except that 10 g of potassium tert.-butylate, 330 g (2.95 mols) of (2,2-dimethyl-propylidene)-allylamine and 450 ml of benzene were used. After a reaction time of 3.5 hours at 40° C., 325 g (2.9 mols), corresponding to a yield of 98.5% of theory, of N-2,2-dimethyl-propylidene-(propenylamine) are obtained as a mixture of the cis/trans isomers in a weight ratio of 66:35; boiling point 110° C.; $n_D^{20}=1.4487$.

EXAMPLE 11

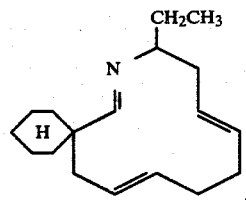

The procedure described in Example 2 is repeated except that 109 g (0.72 mol) of N-propylidene-(cyclohexylidene-methylamine) and 123 g (2.28 mols) of 1,3-butadiene are used. Distillation yields 115 g (0.444 mol) of 3-spiro-cyclohexane-12-ethyl-1-aza-1,5,9-cyclododecatriene; yield 61.6% of theory, based on converted N-propylidene-(cyclohexylidene-methylamine) (conversion 100%); boiling point 103° C./0.03 mm Hg; $n_D^{20}=1.5101$.

Analysis for $C_{18}H_{29}N$ (molecular weight 259): calculated: C, 83.33%; H, 11.27%; N, 5.40%. found: C, 83.4%; H, 11.4%; N, 5.3%.

Mass spectrum: molecular peak 259; fragment masses 230, 216, 176, 150 and 122.

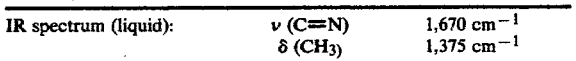

-continued

| | | |
|---|---|---|
| | δ (C=N) H | 960 cm⁻¹. |

The N-propylidene-(cyclohexylidene-methylamine) used in the above example was prepared analogously to the N-propylidene-(2-methyl-propenylamine) according to Example 7 (cf. final paragraph of Example 7) except that 5 g of potassium tert.-butylate, 240 g (1.59 mols) of cyclohexyl-methylidene-allylamine and 250 ml of tetrahydrofuran were used. After a reaction time of 1 hour at 30° C., 199 g (1.32 mols) of N-propylidene-(cyclohexylidene-methylamine) are obtained, corresponding to a yield of 83% of theory; boiling point 51°–53° C./0.3 mm Hg; $n_D^{20}=1.5072$.

EXAMPLE 12

The procedure described in Example 2 is repeated except that 467 g (2.8 mols) of N-propylidene-(2-ethyl-hexen-1-yl-amine), 324 g (6 mols) of 1,3-butadiene, 15.7 g (61 mmols) of nickel acetylacetonate, 7.45 g (60 mmols) of trimethyl phosphite, 23.4 g (180 mmols) of ethoxydiethyl-aluminium and 300 ml of toluene are used. After a reaction time of 4 hours at 40° C., working up as described in Example 2 yields 624 g (2.27 mols) of 3,12-diethyl-3-n-butyl-1-aza-1,5,9-cyclododecatriene as a mixture of isomers; yield 81% of theory, based on the converted N-propylidene-(2-ethyl-hexen-1-yl-amine) (conversion 100%); boiling point 98°–100° C./0.3 mm Hg; $n_D^{20}=1.4905$.

Analysis for $C_{19}H_{33}N$ (molecular weight 275): calculated: C, 82.84%; H, 12.07%; N, 5.08%. found: C, 82.78%; H, 12.33%; N, 5.04%.

Mass spectrum: molecular peak 275; fragment masses 246, 218, 190, 166, 138, 67, 55 and 41.

| IR spectrum (liquid): | ν (C=N) | 1,670 cm⁻¹ |
|---|---|---|
| | δ (CH₃) H | 1,378 cm⁻¹ |
| | δ (C=C) H | 962 cm⁻¹. |

¹H-NMR spectrum τ(ppm): 2.88(s) and 2.93(s), 4.8–5.1(m), 7.3(m), 7.7–8.8(m) and 9.1(m) in a ratio of 1:4:1:18:9.

The N-propylidene-(2-ethylhexen-1-yl-amine) used in the above example was prepared in a manner analogous to that described in the final paragraph of Example 7 except that 10 g of potassium tert.-butylate, 800 g (4.79 mols) of (2-ethyl-hexylidene)-allylamine and 600 ml of tetrahydrofuran were used. After a reaction time of 2 hours at 35° C., 682 g (4.08 mols) of N-propylidene-(2-ethyl-hexen-1-yl-amine) are obtained, corresponding to a yield of 85.2% of theory (mixture of isomers in a weight ratio of 55:45); boiling point 53°–56° C./1 mm Hg; $n_D^{20}=1.4698$.

EXAMPLE 13

710 g (3.93 mols) of N-2-methyl-pentylidene-(2-methyl-penten-1-yl-amine) [prepared by reacting 2-methyl-valeraldehyde with ammonia in accordance with U.S. Pat. Specification No. 2,319,848] and 432 g (8.0 mols) of 1,3-butadiene are reacted by a procedure analogous to that described in Example 12. After working up the reaction mixture, 995 g (3.45 mols) of 3-methyl-3-n-propyl-12-(2-pentyl)-1-aza-1,5,9-cyclododecatriene are obtained as a mixture of isomers (2 main isomers); yield 87.7% of theory, based on the converted N-2-methyl-pentylidene-(2-methyl-penten-1-yl-amine) (conversion 100%); boiling point 103°–105° C./0.3 mm Hg; $n_D^{20}=1.4886$.

Analysis for $C_{20}H_{35}N$ (molecular weight 289.51): calculated: C, 82.97%; H, 12.19%; N, 4.84%. found: C, 83.25%; H, 12.44%; N, 5.01%.

Mass spectrum: molecular peak 289; fragment masses 260, 246, 218, 176, 139 and 110.

¹H-NMR spectrum τ(ppm): 2.94(s), 4.6–5.1(m), 7.4(m), 7.7–8.3(m), 8.65(m), 8.87(s) and 9.07(m) in a ratio of 1:4:1:9:8:3:9.

| IR spectrum (liquid): | ν (C=N) | 1,670 cm⁻¹ |
|---|---|---|
| | δ (CH₃) H | 1,380 and 1,375 cm⁻¹ |
| | δ (C=C) H | 960 cm⁻¹. |

EXAMPLE 14

The procedure described in Example 12 is repeated except that 760 g (3.21 mols) of N-2-ethyl-hexylidene-(2-ethyl-hexen-1-yl-amine) [prepared by reacting 2-ethyl-caproaldehyde with ammonia in accordance with U.S. Pat. No. 2,319,848] and 378 g (7 mols) of 1,3-butadiene are used. After working up the reaction mixture, 930 g (2.69 mols) of 3-ethyl-3-n-butyl-12-(3-heptyl)-1-aza-1,5,9-cyclododecatriene are obtained in the form of a 7:3 mixture of isomers, corresponding to a yield of 84% of theory, based on the converted N-2-ethyl-hexylidene-(2-ethyl-hexen-1-yl-amine) (conversion 100%); boiling point 106°–109° C./0.1 mm Hg; $n_D^{20}=1.4895$.

Analysis for $C_{24}H_{43}N$ (molecular weight 345.62): calculated: C, 83.41%; H, 12.54%; N, 4.05%. found: C, 83.51%; H, 12.78%; N, 4.29%.

Mass spectrum: molecular peak 345; fragment masses 316, 302, 289, 247, 218, 190, 138 and 69.

¹H-NMR spectrum τ(ppm): 2.91(s) and 2.97(s), 4.8–5.15(m), 7.23(m), 7.7–8.3(m), 8.5–8.9(m) and 9.1(m) in a ratio of 1:4:1:8:17:12.

| IR spectrum (liquid): | ν (C=N) | 1,670 cm⁻¹ |
|---|---|---|
| | δ (CH₃) H | 1,377 cm⁻¹ |
| | δ (C=C) H | 964 cm⁻¹. |

EXAMPLE 15

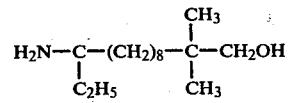

199 g (0.91 mol) of the 3,3-dimethyl-12-ethyl-1-aza-1,5,9-cyclododecatriene prepared according to Example 7 are added dropwise in the course of 15 minutes to a solution of 150 g (1.53 mols) of sulphuric acid in one liter of water. Impurities are removed by a subsequent 20 minute stream distillation. The aqueous sulphuric acid solution is then hydrogenated at normal pressure and 20°–25° C. in the presence of a platinum-on-charcoal catalyst (5% by weight of platinum) with the absorption of 3 mols of hydrogen, to give 2,2-dimethyl-11-ethyl-11-aminoundecanol. After filtering off the catalyst, the aqueous solution is neutralised with concentrated sodium hydroxide solution and the amino-alcohol which separates out is extracted by shaking with toluene and distilled. 149 g (0.613 mol) of 2,2-dimethyl-11-ethyl-11-aminoundecanol are obtained, corresponding to a yield of 67.4% of theory; boiling point 118° C./0.05 mm Hg; $n_D^{20} = 1.4656$.

The above amino-alcohol was tested to determine its fungicidal action, in particular its action against *Cercospora personata* (=*C. arachidicola*) on groundnut plants:

3-week old groundnut plants were sprayed with a spray liquor (0.02% by weight of active substance) prepared from a wettable powder of the active ingredient. After about 12 hours, the treated plants were dusted with a conidia suspension of the fungus. The infected plants were then incubated for about 24 hours at >90% relative atmospheric humidity and then placed in a greenhouse at about 22° C. The infestation with fungi was evaluated after 12 days.

Compared with an untreated control, plants which were treated with the above active ingredient had a low infestation with fungi.

What is claimed is:

1. A compound of the formula I

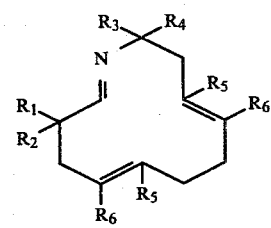
(I)

in which $R_1$ and $R_3$ independently of one another are hydrogen or alkyl having 1–8 C atoms and $R_2$ and $R_4$ independently of one another are alkyl having 1–8 C atoms, or $R_1$ and $R_2$ and/or $R_3$ and $R_4$ together with the bonding C atom form cycloalkyl having 5–8 C atoms, and $R_5$ and $R_6$ independently of one another are hydrogen or alkyl having 1–4 C atoms.

2. A compound of the formula I according to claim 1, in which $R_5$ and $R_6$ are each hydrogen, $R_1$ and $R_3$ independently of one another are hydrogen or alkyl having 1–5 C atoms, $R_2$ is alkyl having 1–5 C atoms and $R_4$ is alkyl having 1–7 C atoms, or in which $R_3$, $R_5$ and $R_6$ are each hydrogen, $R_1$ and $R_2$ together with the bonding C atom are cyclopentyl or cyclohexyl and $R_4$ is alkyl having 1–7 C atoms.

3. A compound of the formula I according to claim 1, in which $R_3$, $R_5$ and $R_6$ are each hydrogen, $R_1$ and $R_2$ independently of one another are alkyl having 1–4 C atoms or together with the bonding C atom are cyclohexyl, and $R_4$ is alkyl having 1–7 C atoms.

4. A compound according to claim 1, which is 3,3-dimethyl-12-isopropyl-1-aza-1,5,9-cyclododecatriene.

5. A compound according to claim 1, which is 3,3-dimethyl-12-ethyl-1-aza-1,5,9-cyclododecatriene.

6. A compound according to claim 1, which is 3,12,12-trimethyl-1-aza-1,5,9-cydododecatriene.

7. A compound according to claim 1, which is 3-spiro-cyclohexane-12-ethyl-1-aza-1,5,9-cyclododecatriene.

8. A compound according to claim 1, which is 3-methyl-3-n-propyl-12-(2-pentyl)-1-aza-1,5,9-cyclododecatriene.

9. A process for the preparation of a compound of the formula I according to claim 1, which comprises reacting an aza-butadiene of the formula II

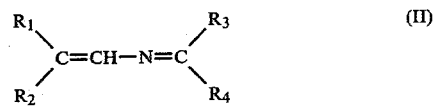
(II)

in which $R_1$ to $R_4$ are as defined in claim 1, in the presence of a catalyst which is a nickel-(O) complex of a diene of the formula III, obtained by the reduction of a carbonyl-free nickel compound in the presence of a diene of the formula III in the presence or absence of an electron donor ligand selected from the group consisting of alkyl phosphines, aryl phosphines, alkyl phosphites, aryl phosphites, alkyl argines, aryl arsines, alkyl antimonys and aryl antimonys, at a temperature between about −40° C. and 150° C. with a compound of the formula III

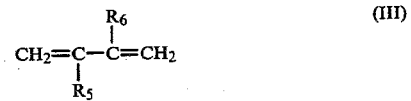
(III)

in which $R_5$ and $R_6$ are as defined in claim 1.

10. A process according to claim 9, which comprises carrying out the reaction at a temperature between +40° C. and +110° C.

* * * * *